(12) United States Patent
Berger et al.

(10) Patent No.: US 7,807,138 B2
(45) Date of Patent: Oct. 5, 2010

(54) BIOMARKERS OF METABOLIC RESPONSES TO HEPATIC DRUGS

(75) Inventors: Alvin Berger, Raleigh, NC (US); Imran A. Shah, Chapel Hill, NC (US)

(73) Assignee: Metabolon, Inc., Durham, NC (US)

( * ) Notice: Subject to any disclaimer, the term of this patent is extended or adjusted under 35 U.S.C. 154(b) by 16 days.

(21) Appl. No.: 11/840,466

(22) Filed: Aug. 17, 2007

(65) Prior Publication Data

US 2008/0213745 A1 Sep. 4, 2008

Related U.S. Application Data

(60) Provisional application No. 60/838,562, filed on Aug. 17, 2006.

(51) Int. Cl.
*A61N 49/00* (2006.01)
(52) U.S. Cl. ...................................................... 424/9.2
(58) Field of Classification Search ...................... 435/4; 424/9.2
See application file for complete search history.

(56) References Cited

U.S. PATENT DOCUMENTS

2003/0170643 A1* 9/2003 Fisher et al. .................. 435/6
2004/0265889 A1* 12/2004 Durham et al. ................ 435/6
2006/0275816 A1* 12/2006 Henderson et al. ............ 435/6
2008/0176266 A1  7/2008 Berger et al.

OTHER PUBLICATIONS

Chinetti-Gbaguidi G. et al. Measuring Biomarkers to Assess the Therapeutic Effects of PPAR Agonists. Pharmacogenomics 8(11)1567-1580, Nov. 2007.*
Ringeissen S. et al. Potential Urinary and Plasma Biomarkers . . . Biomarkers 8(3-4)240-271, May-Aug. 2003.*
Berger, A., et al., "Dietary effects of arachidonate-rich fungal oil and fish oil on murine hepatic and hippocampal gene expression", Lipids in Health and Disease, 1(2), 1-23 (2002).
Gonzalez, F. et al., "Mechanism of action of the nongenotoxic peroxisome proliferators: Role of the peroxisome proliferator-activated receptor α", Journal of the National Cancer Institute, 90(22), 1702-1709 (1998).
Hamadeh, H. et al., "Gene expression analysis reveals chemical-specific profiles", Toxicological Sciences, 67, 219-231 (2002).

* cited by examiner

*Primary Examiner*—Ralph Gitomer
(74) *Attorney, Agent, or Firm*—Brinks Hofer Gilson & Lione

(57) ABSTRACT

Methods for the measurement and prediction of response to hepatotoxicants and carcinogens through the detection of metabolites in a mammal are provided. The metabolites can be used as biomarkers, including efficacy biomarkers, surrogate biomarkers, and toxicity biomarkers. The methods find use for early prediction of toxicity, target identification/validation, and monitoring of drug efficacy.

6 Claims, No Drawings

BIOMARKERS OF METABOLIC RESPONSES TO HEPATIC DRUGS

CROSS-REFERENCE TO RELATED APPLICATIONS

This application claims the benefit of U.S. Provisional Application No. 60/838,562, filed Aug. 17, 2006, the entirety of which is hereby incorporated by reference.

STATEMENT REGARDING FEDERALLY SPONSORED RESEARCH

This invention was made with United States Government support under SBIR Phase 1 Contract #: 291200445524C (SBIR Phase 1 Contract Solicitation PHS-2004-1-100) awarded by the National Institute of Environmental Health Sciences (NIEHS). The United States Government has certain rights in the invention.

FIELD

The invention relates generally to methods of measuring metabolic responses to hepatotoxicants and carcinogens.

BACKGROUND

Hepatotoxicants and carcinogens have been studied for metabolic effect prior to the omic era, and more recently using microarray transcriptomic technology. While the latter approach has greatly expanded knowledge of such compounds, transcriptomic approaches do not actually measure the metabolites (small molecules) and pathways perturbed.

For example, clofibrate is a fibrate type of hypolipidemic drug, and also a hepatotoxicant and carcinogen. It acts on peroxisome proliferator activated receptor alpha (PPARα) receptors. Peroxisome proliferator activated receptors (PPARs) are nuclear hormone receptors that are activated by micromolar concentrations of lipids, fibrates and thiazolidinediones. This subfamily can be divided into three isotypes, designated PPARα, δ, and γ, each with tissue-specific expression. PPARα receptors are particularly abundant in rodents, but are also present in humans. In humans, PPARγ predominates over PPARα, and hepatocyte nuclear factor (HNF) has some similar functions as PPARα in rodents, but both PPAR types are present in rodents and humans. Clofibrate (ethyl-p-chloro-phenoxyisobutyrate; CAS 637-07-0)) is a fibrate type of hypolipidemic (cholesterol lowering) drug, which is also a hepatotoxicant and carcinogen at high levels. It acts predominately on PPARα receptors.

Clofibrates work by activating PPARs, which in turn form heterodimers with retinoid X receptor (RXR), and interact with the peroxisome proliferator response element (PPREs) in gene promoters. PPREs are direct repeats (DR) of a hexanucleotide sequence AGGTCA separated by one nucleotide and are therefore referred to as a DR-1 response element. PPARα and PPARγ play critical roles in the catabolism and storage of fatty acids, whereas the function of PPARδ is less certain. PPARα is the predominant PPAR subtype expressed in liver.

The overall effects of clofibrate are to decrease fat synthesis and increase fat degradation; and to decrease glycolysis and increase gluconeogenesis. In essence, clofibrate mimics the fasted metabolic state. Other effects of clofibrate observed in some studies are: increased oxidative stress; increased cell replication; and increased spontaneous preneoplastic lesions. Short term treatment of clofibrate may not induce transcriptional events as efficiently or at all, as no DNA adducts have been observed. Gonzalez et al. (1998) *J Natl Cancer Inst* 90: 1702-1709. PPARα regulates genes involved in fatty acid transport, synthesis and oxidation, glucose and lipid metabolism, ketogenesis and Δ5, Δ6, and Δ9-desaturation of fatty acids. Specific genes altered by clofibrate, with possible PPREs are described in Berger et al. (2002) *Lipids Health Dis* 1: 2 and Hamadeh et al. (2002) *Toxicol Sci* 67: 219-231.

Clofibrate has been studied at high doses for various durations for its hepatotoxic and carcinogenic effects with microarrays, thus providing a putative map of how clofibrate may affect metabolism. In one study, rats exposed to clofibrate were monitored over time by a combination of histopathology and a transcriptomic approach. After 24 h, there were no microscopic changes to liver after a single exposure of clofibrate or other toxicants. In contrast, after 2 weeks, clofibrate induced hypertrophy. Although a similar set of genes was modified under both conditions, pattern recognition could distinguish the different drug treatments.

These studies demonstrate the predictive biomarker potential of hepatic transcriptomics with respect to liver histopathology changes in response to exposure to hepatotoxicants and carcinogens. Nonetheless, such approaches fail to actually measure the metabolites and pathways perturbed. Thus, there is a need for readily accessible biomarkers of exposure to hepatotoxicants and carcinogens (i.e., biomarkers present in serum, blood, or saliva).

SUMMARY

Methods are provided for the measurement and prediction of response to hepatotoxicants and carcinogens through the detection of metabolites in a mammal. Such metabolites are useful as biomarkers, including efficacy biomarkers, surrogate biomarkers, and toxicity biomarkers.

In one embodiment, the metabolites are obtained from tissue. In one embodiment, the metabolites are obtained from a bodily fluid. In one embodiment, the metabolites are obtained from liver. In one embodiment, the metabolites are obtained from blood. In one embodiment, the metabolites are obtained from serum.

DETAILED DESCRIPTION

Methods are provided for determining exposure of a cell or cells to a chemical compound. In one embodiment, the method comprises the steps of measuring a biomarker panel of one or more metabolites in a sample taken from cell or cells; combining the measurements for the metabolites using a mathematical function including the measurements; and obtaining and analyzing an output from the function, wherein the output of the function is indicative of exposure to the chemical compound. In one embodiment, the chemical compound is a hepatotoxicant. In one embodiment, the chemical compound is a carcinogen through the detection of metabolites. In one embodiment, the cell or cells are in vivo. In one embodiment, the cell or cells are in vitro. In one embodiment, the cell or cells are mammalian.

Methods are also provided for constructing the function from a dataset comprising metabolite measurements taken from a plurality of samples. The samples may be from groups displaying differing phenotypes, or from groups subject to differing doses or times of exposure to a chemical compound. In one embodiment, the function is constructed by a statistical method followed by a step of performance evaluation. In one embodiment, the function is obtained by multivariate analysis of the dataset. Techniques of multivariate analysis are known and are discussed in Dillon & Goldstein, *Multivariate Analysis: Methods and Applications*, John Wiley & sons, New York (1984) and Duda, Hart, & Stork, *Pattern Classification*, 2d ed., John Wiley & Sons, New York (2000), each of which is incorporated herein by reference in its entirety. Performance of the function can be evaluated by various statistical methods. The output of such a method is metabolites that can serve as biomarkers, including efficacy biomarkers, surrogate biomarkers, and toxicity biomarkers.

The metabolites are detected using analytical chemistry techniques, including mass spectrometry. In one embodiment, the metabolites are detected using gas chromatograph-mass spectrometry (GC-MS). In one embodiment, the metabolites are detected using liquid chromatograph-mass spectrometry (LC-MS). GC-MS techniques are known in the art, including without limitation Quadrupole GC-MS, Ion-trap GC-MS, Time-of Flight GC-MS, Sector GC-MS, etc. LC-MS techniques are known in the art, including without limitation Quadrupole Triple LC-MS, Quadrupole LC-MS, 3D-Ion-trap LC-MS, Linear Iontrap LC-MS, Time-offlight LC-MS, Quadrupole-Time-offlight LC-MS Hybrid LC-MS, Sector LC-MS, FT-ICR LC-MS, etc. MALDI-TOF MS techniques are known in the art, including without limitation Linear only MALDI-TOF MS, Linear and/or Reflectron MALDI-TOF MS, TOF-TOF MALDI-TOF MS, etc. Such techniques are reviewed in Burlingame et al. (2000) *Mass Spectrometry In Biology & Medicine* Totowa, N.J., Humana Press; Niessen (2001) *Current Practice Gas Chromatography—Mass Spectrometry*, Marcel Dekker Inc., New York, N.Y.; W. Niessen (1998) *Liquid Chromatography—Mass Spectrometry* 2d Ed., Marcel Dekker Inc., New York, N.Y.; and Imma Ferrer et al., American Chemical Society (2003) *Liquid Chromatography/Mass Spectrometry MS/MS and Time of Flight MS: Analysis of Emerging Contaminants*, each of which are incorporated by reference herein in their entirety. As is known to those of skill in the art, the output of mass spectrometry is a peak characteristic of a given chemical compound or compounds (including metabolites). Until it is assigned an identity, each mass spectrometry is termed a component.

In one embodiment, the hepatotoxicant is clofibrate. Clofibrate or vehicle is administered orally (0, 50, 250 mg/kg/d) to groups of 6 rats and serum and livers are collected 6 and 24 h after either a single or 14 daily doses. Global biochemical profiles are determined by LC-MS and GC-MS and components highly perturbed by clofibrate exposure are identified by the methods described above. One or more of the biomarkers identified in the present methods may be utilized as biomarkers of clofibrate exposure. These are provided in Table 1.

TABLE 1

Fold changes for hepatic biomarkers, in rats exposed to 50 and 250 mg/kg/d for 14 days, LCMS data.

| | H after administration of drug | | | |
|---|---|---|---|---|
| | 6 H | | 24 H | |
| | Fold changes relative to control | | | |
| | 50/C | 250/C | 50/C | 250/C |
| Creatine | | 1.4 | | 2.1 |
| D-Glycerate | 1.3 | 1.2 | | |
| Serine | | 1.3-1.7 | | 1.7 |
| Hypotaurine | | 1.3 | | 1.3 |
| Ornithine | | 2.3-5.4 | 1.84 | 2.8-10.6 |
| Glutathione | | −1.5 | | |
| Glycero-3-phosphoethanolamine | | | −3.2 | −7.7 |
| Threonate | | 1.3 | | −1.4 |
| Uracil | | −1.1--3.5 | | |
| Various bile acids | | | 1.4 | 1.3 |

In one embodiment, the metabolites correlate with drug efficacy. Clofibrate, for example, acts on PPARα and has hypolipidemic effects. Clofibrate acts to decrease fat synthesis, increase fat degradation, decrease glycolysis and increase gluconeogenesis. Metabolites changing via PPARα cascades are potential efficacy markers. Using the present methods, metabolites were identified that changed with clofibrate exposure. These metabolites are set forth in Table 2.

TABLE 2

Hepatic efficacy biomarkers identified by GC in rats exposed to 250 mg/kg/d (fold change)

| | | NIST | DAY 1 | | DAY 14 | |
|---|---|---|---|---|---|---|
| CLASS | Compound Name | SIMILARITY SCORE | 6 H | 24 H | 6 H | 24 H |
| Amino acid | Glycine | 846 | 2.69** | 3.42* | | |
| | l-Alanine | 907 | | 4.74* | | |
| | L-Aspartic acid | 831 | | 27.88*** | | |
| Fatty Acid | Palmitate | 898 | 0.95*** | | 0.72** | |
| | Stearate | 856 | 1.07* | | | |
| | Linoleic acid | 914 | 0.97* | | | |
| | Arachidonic acid | 921$^a$ | | | 0.22*** | |
| | Docosahexaenoic acid | 826 | | | | 0.58* |
| Carbohydrate Metabolism | Glucose (aq) | 898 | 0.29* | | | 0.39** |
| | Lactic acid | 930 | 1.56** | 4.41* | | |
| | Succinic acid (Butanedioic acid) | 857 | | 17.05** | | |
| | Malate | 747 | | | 0.1** | 0.33** |

TABLE 2-continued

Hepatic efficacy biomarkers identified by GC in rats exposed to 250 mg/kg/d
(fold change)

| CLASS | Compound Name | NIST SIMILARITY SCORE | DAY 1 6 H | DAY 1 24 H | DAY 14 6 H | DAY 14 24 H |
|---|---|---|---|---|---|---|
| MAG metabolism | Glycerol 1(3)-phosphate | 879 | | 2.56* | | |
| | 1-Mono palmitoylglycerol | 849 | 0.91** | | 0.04** | |
| | 1-Mono stearoylglycerol | 838 | | 17.14** | 0.22** | |
| | 2-Mono stearoylglycerol | 807 | | | 0.41* | |
| | 1-Mono oleoylglycerol | Manual | 0.98* | | | |
| | 2-Mono oleoylglycerol | 799 | 1.12*** | | | |
| | 1-Mono linoleoylglycerol | Manual | 1.11*** | | | |
| Sterol | Cholesterol | 864$^a$ | 1.34*** | | 1.87** | 0.69** |
| | β-Sitosterol | 746$^a$ | | | 0.37** | 0.46* |
| Clofibrate metabolite | Propanoic acid, 2-(4-chlorophenoxy)-2-methyl- | 869 | (not present in control) | | | |

In one embodiment, methods are provided for the characterization of clofibrate efficacy through the detection of metabolites. Because clofibrate is itself a PPAR activator, these metabolites are useful as biomarkers of PPAR activators.

Because the biomarkers provided in Table 2 correlate with efficacy, they are useful in methods for separating on-target from off-target drug effects through the detection of metabolites.

The following examples are offered by way of illustration and not by way of limitation.

EXAMPLES

Example 1

Design of Clofibrate Studies

A. Study 1:

Rats (6 per group) were dosed by gavage with vehicle, 50 or 250 mg/kg clofibrate per day for 1 (single dose) or 14 days (repeated dose). These groups are referred to as "day 1" and 'day 14 (d 1 and d14)." Liver and serum were collected at 6 and 24 h post-dosing in the day 1 and day 14.

In detail, a single dose of clofibrate or vehicle was administered by gavage (0, 50 and 250 mg/kg) to groups of 18 male Sprague Dawley rats at 11 wks age. Six rats per dose group were euthanized at 6 and 24 h post-dose. Serum (for metabolomics and alanine aminotransferase (ALT), and aspartate aminotransferase (AST)), liver lobes (for histology), and frozen liver and urine (for metabolomics) were collected. Six rats per dose group were placed in metabolism cages for urine collection at −24-0 h, 0-6 h, 6-24 h and 24-48 h. These rats were removed from metabolism cages at 48 h post-dose, for blood and liver collection. The detailed study design is set forth in Chart 1.

CHART 1

Detailed study design

| Study designation in protocol | Organ | # Rats/group | Doses clofibrate (0, 50, 250) | Details of Time pts | Total |
|---|---|---|---|---|---|
| Single exposure study (1 injection in 1 d) | | | | | |
| study 1 (d1) | liver | 6 | 3 | 6 h, 24 h after dosing | 36 |
| study 2 (d1) | liver | 6 | 3 | 48 h | 18 |
| study 1 (d1) | plasma | 6 | 3 | 6, 24 h | 36 |
| study 2 (d1) | plasma | 6 | 3 | 48 h | 18 |
| study 2 (d1) | urine | 6 | 3 | −24-0 (baseline), 0-6, 6-24, 24-48 | 72 |
| Repeated exposure study (13 injections in 14 d, measurements over last 2 d) | | | | | |
| study 1 (d14) | liver | 6 | 3 | 14 d + 6 h, 14 d + 24 h, | 36 |
| study 2 (d14) | liver | 6 | 3 | 14 d + 48 h | 18 |
| study 1 (d14) | plasma | 6 | 3 | 14 d + 6 h, 14 d + 24 h, | 36 |
| study 2 (d14) | plasma | 6 | 3 | 14 d + 48 h | 18 |
| study 2 (d14) | urine | 6 | 3 | 14 d + 6 h (0-6), 14 d + 24 h (6-24), 14 d + 48 h (24-48) | 54 |

B. Study 2:

Another group of rats received 14 repeated daily gavaged doses (0, 50 and 250 mg/kg) of vehicle or clofibrate. These rats were transferred to metabolism cages following administration of either 1 or 13 doses of clofibrate at 50 mg/kg, 250 mg/kg, or by vehicle. Urine was collected at various time points (Chart 1). Urine was not collected at time point −24-0 (baseline) at day 14 (see study 2 (d 14)). The protocol was nearly identical to the single dose experiment.

Example 2

Sample Preparation and Evaluation

Samples were extracted with 20% acetonitrile, then were evaporated and re-constituted in distilled water. For the liver, the left lobe was selected for metabolomic analysis.

Liver enzymes: ALT and AST were not elevated in any groups.

Histology: After a single dose, there was a dose related increase and severity of hepatocellular mitotic figures as dose increased from 50 to 250-mg/kg. After 14 doses at 250 mg/kg/day, hepatocellular cytologic alterations (indicating loss of glycogen and eosinophilic granular cytoplasm) were noted at all time points.

Example 3

Metabolomics

LC-MS was performed in positive and negative electrospray ionization modes on Bruker time of flight (TOF) instruments, using Icoria™ proprietary HPLC methods and picking and alignment programs. Samples were randomly placed in wells on 96-well plates, keeping d 1 and d 14 samples on separate plates. Between 54 and 72 samples plus quality control samples were run on each plate. Pre- and post-flight instrument checks were carried out. Thereafter, data integrity checks were performed to detect any errors related to our Laboratory Information Management System (LIMS) system, labeling of samples, and missing or extraneous information.

Example 4

Identifying Early Metabolic Response to Clofibrate Exposure

Based on natural groupings of subjects, we identified metabolomic components perturbed at 6 h and returned to baseline at 24 h. Table 1 (set forth in the Detailed Description, above) shows the components at each dose and time point with significant increases and decreases relative to vehicle treated subjects.

For GC-MS, liver was extracted with CHCl3:MeOH mixtures. Organic residue was derivitized with BSTFA and dried aqueous residues were derivitized with methoxyamine HCl/BSTFA. Samples were injected with 10:1 split into an Agilent 6890 gas chromatograph. A Leco Pegasus III TOFMS was used. Ions were generated at 70 eV with 3.2 mA ionization current; 25 spectra/s were recorded for 60-800 m/z. Acceleration voltage activated after 180 solvent delay. Detector voltage: 1750 V. Data were processed with Leco ChromaTOF software. Automatic peak detection and mass spectrum deconvolution were performed using 1.33 s peak width. Peaks with S/N less than 20 were rejected. Component identification was accomplished with the NIST 98' MS library and, in some cases, verified with standards. Components with similarity greater than 600 were used for analysis. The results of the statistical analysis are shown in Table 2, above, in the Detailed Description.

Example 5

Computational and Statistical Procedures

The quality of the metabolomic data is visually assessed through the distribution of the coefficient of variation for each aligned LC-MS component across technical replicates and the reproducibility of the metabolomic profiles is evaluated by clustering the technical (machine) replicates. A component represents a single molecule or a group of molecules with very similar structural similarity (e.g., an isomer) that bin together on the m/z-retention time grid during alignment of peaks. A technical replicate refers to an aliquot of the same sample plated on different wells of a plate, in random fashion (as opposed to an independent extraction of the same sample).

Trends between dose and time points, for serum and liver, were assessed using two techniques. First, principal components analysis (PCA) is used to visually assess biological variability (as proposed originally). Furthermore, an unbiased quantitative assessment of the separation between the subjects in each dose-time group is conducted using an unsupervised learning approach based on hierarchical agglomerative clustering of the metabolomic profiles for the subjects.

T-tests were conducted to identify the significantly perturbed components in the liver and the serum of subjects at each time post-dose by comparison against the control subjects (vehicle control group). F-tests were conducted to identify those metabolomic components that were significantly perturbed in response to dose, time, and dose-time interaction.

Metabolites associated with LC-MS components were putatively identified using our proprietary database of mammalian metabolites as well as external sources of metabolic information.

Example 6

Identification

A series of standards were run and their retention time, m/z, and intensity were stored in a database of components. Components identified above were then compared to this known component database. Additionally, internal and external compound databases (Brenda, Kegg, ChemFinder) were queried for similarities in exact mass, and then to eliminate xenobiotic molecules or molecules that were not reasonable from a polarity perspective.

Example 7

LCMS Metabolomic Data Generation

LC-MS peaks from each sample were aligned by mass to charge (m/z) ratio and retention time (RT) across all samples for each matrix, and quantified using Icoria's proprietary software. LC-MS components for each replicate of each sample were represented mathematically as a vector. Each component in each sample has three associated measurements: raw intensity in each sample; chromatographic retention time for peaks; and the mass divided by the charge (M/z). The metabolomic profile of each sample (denoted as x) is defined by the set of all components of known intensity, retention time and mass divided by charge. Before analyzing the data for the following preprocessing steps are carried out:

Step 1. Normalization to internal standard: Each metabolomic profile, x, is normalized using the intensity of a standard compound (called the 'internal standard', which is added to each sample), transforming x into a relative intensity profile. This step is necessary to address the systematic variation of raw intensity measurements between samples due to instrument signal fluctuation. For this purpose, the internal standard need not be chemically and structurally related to the metabolites of interest. Three internal standard are added to each matrix and the internal standard giving the most consistent responses (best separation in m/z axis, less matrix suppression, best peak shapes, etc.) is selected. These are d3 methionine for liver and serum, and d5 tryptophan for urine.

Step 2. Technical variability and average metabolomic profile: The technical (machine) replicate variation in components is measured using the coefficient of variation, CV, of the relative intensities (where $$CV_{jk} = \frac{\sigma_{jk}}{\mu_{jk}},$$

where $\sigma_{jk}$=standard deviation of component k in sample j, $\mu_{jk}$=mean of component k in sample j). The mean value of the relative intensity, $\mu_{jk}$, for each component is used to build the average metabolomic profile for each subject.

Step 3. Missing value correction: Components that are not observed across the three machine replicates are treated stringently, using deletion. If the component is observed across all replicates, $\mu_{jk}$ is calculated using three relative intensity values. When the component is observed in only two subjects, $\mu_{jk}$ is calculated between two observed values. When the component is only observed in one replicate, $\mu_{jk}$ is set to the limit of detection (a low intensity value).

Step 4. Distribution of relative intensity and log transformation: Though the literature on the intensity distribution of metabolomic data is limited, in our studies we have found this close to the lognormal probability density function. There are two main reasons to consider this transformation. Biologically, this transformation enables consideration of low concentration metabolites that capture subtle but important effects. Statistically, this transformation is important for measuring the similarity between the biochemical profiles of samples (through a distance metric). Hence, we analyze the intensity distribution in the biochemical profiles of the samples for skewness visually and transform logarithmically (base e and 10) if it is lognormal.

Step 5. Data quality: clustering of technical replicates: In addition to the quality control procedures described in Section IV. B, we assessed quality of replication by comparing metabolomic profiles for each subject from each tissue by using hierarchical agglomerative clustering using Pearson correlation as the distance metric.

Example 8

Dose and Temporal Data Trends

An unbiased grouping of subjects using liver and serum data for days 1 and 14 is analyzed as described in the following paragraphs.

Dose and Time Effects Studied with PCA

Dose and time effects are first studied with PCA to visually assess data groupings.

Effects of Dose and Time Studied with Hierarchical Clustering

Hierarchical agglomerative clustering is used with Ward's minimum variance method, with correlation as the distance metric to discover natural data groupings. Generally, subclusters separated by dose and time. The two principal clusters for each day and time are described below.

Comparisons Between PCA and Clustering Results

The overall groupings are consistent between PCA and clustering analysis. Following single and multiple exposure to clofibrate, the control and low dose rats grouped together with subgroupings based on dose and time. High dose rats grouped separately. Rats exposed to clofibrate appeared to recover more after 24 h than after 6 h, and recovery is likely more pronounced following chronic exposure, suggesting adaptation (more efficient break down of drug, better clearance of drug, homeostatic mechanisms).

Effects of Dose and Time Studied with GLM Statistical Approach

Effects of dose, time, and dose-time interaction are studied with a Generalized Linear Model (GLM) statistical approach. The significance of dose, time and dose*time effects is analyzed per component for d 1 and d 14 serum and liver. The two main experimental factors are dose and time. There are three dose levels (0, 50, and 250 mg/kg) and two time levels (6, 24 h), yielding six treatments.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of determining the efficacy of clofibrate on a subject, the method comprising:

analyzing a biological sample from the subject to determine the level(s) of one or more biomarkers for efficacy selected from the group consisting of glycine, 1-alanine, L-aspartic acid, palmitate, stearate, linoleic acid, arachidonic acid, docosahexanoic acid, lactic acid, succinic acid, malate, glycerol-1(3)-phosphate, 1-mono palmitoylglycerol, 1-mono stearoylglycerol, 2-monostearoylglycerol, 1-mono oleoylglycerol, 2-mono oleoylglycerol, 1-mono linoleoylglycerol, β-sitosterol, 2-(4-chlorophenoxy)-2-methyl-propanoic acid, and combinations thereof;

comparing the level(s) of the one or more biomarkers in the sample to levels of the one or more biomarkers from a control sample exposed to efficacious level(s) of clofibrate; and determining whether clofibrate is efficacious in a subject.

2. The method of claim 1, wherein the subject is a mammal.

3. The method of claim 2, wherein the mammal is a human.

4. A method of determining the efficacy of a peroxisome proliferator activated receptor (PPAR) affecting drug on a subject, the method comprising:

analyzing a biological sample from the subject to determine the level(s) of one or more biomarkers for efficacy selected from the group consisting of glycine, 1-alanine, L-aspartic acid, palmitate, stearate, linoleic acid, arachidonic acid, docosahexanoic acid, lactic acid, succinic acid, malate, glycerol-1(3)-phosphate, 1-mono palmitoylglycerol, 1-mono stearoylglycerol, 2-monostearoylglycerol, 1-mono oleoylglycerol, 2-mono oleoylglycerol, 1-mono linoleoylglycerol, β-sitosterol, 2-(4-chlorophenoxy)-2-methyl-propanoic acid, and combinations thereof;

comparing the level(s) of the one or more biomarkers in the sample to levels of the one or more biomarkers from a control sample exposed to efficacious level(s) of clofibrate; and determining whether the PPAR affecting drug is efficacious in a subject.

5. The method of claim 4, wherein the subject is a mammal.

6. The method of claim 5, wherein the mammal is a human.

\* \* \* \* \*